United States Patent
Ragusa (10) Patent No.: US 10,758,652 B2
(45) Date of Patent: Sep. 1, 2020

(54) SYSTEM AND METHOD FOR COLLECTING PLASMA

(71) Applicant: Haemonetics Corporation, Braintree, MA (US)

(72) Inventor: Michael Ragusa, Hingham, MA (US)

(73) Assignee: Haemonetics Corporation, Boston, MA (US)

(*) Notice: Subject to any disclaimer, the term of this patent is extended or adjusted under 35 U.S.C. 154(b) by 539 days.

(21) Appl. No.: 15/608,183

(22) Filed: May 30, 2017

(65) Prior Publication Data

US 2018/0344910 A1 Dec. 6, 2018

(51) Int. Cl.
*A61M 1/02* (2006.01)
*A61M 1/36* (2006.01)
(Continued)

(52) U.S. Cl.
CPC ............ *A61M 1/024* (2013.01); *A61M 1/029* (2013.01); *A61M 1/3672* (2013.01); *A61M 1/38* (2013.01);
(Continued)

(58) Field of Classification Search
CPC .... A61M 1/024; A61M 1/029; A61M 1/3672; A61M 1/3693; A61M 1/38; A61M 2202/0415; A61M 2230/207; G01N 15/05; G01N 2015/055; G01N 15/042; G01N 33/86
See application file for complete search history.

(56) References Cited

U.S. PATENT DOCUMENTS

| | | | |
|---|---|---|---|
| 1,025,059 | A | 4/1912 | Hatton et al. |
| 1,611,725 | A | 12/1926 | Degerth et al. |

(Continued)

FOREIGN PATENT DOCUMENTS

| | | |
|---|---|---|
| CN | 2735985 Y | 10/2005 |
| EP | 0128683 A2 | 12/1984 |

(Continued)

OTHER PUBLICATIONS

Haemonetics Nomogram—Male, 2 pages, May 1990.
(Continued)

*Primary Examiner* — Leslie R Deak
(74) *Attorney, Agent, or Firm* — McCarter & English LLP; Jonathan C. Lovely (57) ABSTRACT

A method for collecting plasma includes determining the weight and hematocrit of a donor, and inserting a venous-access device into the donor. The method then withdraws blood from the donor through a draw line connected to a blood component separation device, and introduces anticoagulant into the withdrawn blood. The blood component separation device separates the blood into a plasma component and a second blood component, and the plasma component is collected from the blood component separation device and into a plasma collection container. The method may then calculate (1) a percentage of anticoagulant in the collected plasma component, and (2) a volume of pure plasma collected within the plasma collection container. The volume of pure plasma may be based, at least in part, on the calculated percentage of anticoagulant. The method may continue until a target volume of pure plasma is collected within the plasma collection container.

20 Claims, 4 Drawing Sheets

(51) Int. Cl.
*A61M 1/38* (2006.01)
*G01N 15/05* (2006.01)

(52) U.S. Cl.
CPC ... *A61M 1/3693* (2013.01); *A61M 2202/0415* (2013.01); *A61M 2230/207* (2013.01); *G01N 15/05* (2013.01); *G01N 2015/055* (2013.01)

(56) References Cited

U.S. PATENT DOCUMENTS

| | | |
|---|---|---|
| 2,087,778 A | 7/1937 | Nelin |
| 2,661,150 A | 12/1953 | Abbott, Jr. |
| 2,750,107 A | 6/1956 | More |
| 2,792,172 A | 5/1957 | Tait |
| 3,096,283 A | 7/1963 | Hein |
| 3,145,713 A | 8/1964 | Latham, Jr. |
| 3,239,136 A | 3/1966 | Hein |
| 3,244,362 A | 4/1966 | Hein |
| 3,244,363 A | 4/1966 | Hein |
| 3,409,213 A | 11/1968 | Latham, Jr. |
| 3,456,875 A | 7/1969 | Hein |
| 3,489,145 A | 1/1970 | Judson et al. |
| 3,565,330 A | 2/1971 | Latham, Jr. |
| 3,655,058 A | 4/1972 | Novak |
| 3,737,096 A | 6/1973 | Jones et al. |
| 3,774,840 A | 11/1973 | Boatright |
| 3,987,961 A | 10/1976 | Sinn et al. |
| 4,007,871 A | 2/1977 | Jones et al. |
| 4,010,894 A | 3/1977 | Kellogg et al. |
| 4,014,497 A | 3/1977 | Spiewok et al. |
| 4,040,965 A | 8/1977 | Kohlheb |
| 4,056,224 A | 11/1977 | Lolachi |
| 4,082,217 A | 4/1978 | Westberg |
| 4,086,924 A | 5/1978 | Latham, Jr. |
| 4,140,268 A | 2/1979 | Lacour |
| 4,142,670 A | 3/1979 | Ishimaru et al. |
| 4,151,844 A | 5/1979 | Cullis et al. |
| 4,197,847 A | 4/1980 | Djerassi |
| 4,285,464 A | 8/1981 | Latham, Jr. |
| 4,300,717 A | 11/1981 | Latham, Jr. |
| 4,303,193 A | 12/1981 | Latham, Jr. |
| 4,321,921 A | 3/1982 | Laszczower |
| 4,387,848 A | 6/1983 | Kellogg et al. |
| 4,425,114 A | 1/1984 | Schoendorfer et al. |
| 4,430,072 A | 2/1984 | Kellogg et al. |
| 4,447,221 A | 5/1984 | Mulzet |
| 4,457,747 A | 7/1984 | Tu |
| 4,464,167 A | 8/1984 | Schoendorfer et al. |
| 4,466,888 A | 8/1984 | Verkaart |
| 4,482,342 A | 11/1984 | Lueptow et al. |
| 4,490,135 A | 12/1984 | Troutner |
| 4,530,691 A | 7/1985 | Brown |
| 4,534,863 A | 8/1985 | Bacon et al. |
| 4,643,714 A | 2/1987 | Brose |
| 4,647,279 A | 3/1987 | Mulzet et al. |
| 4,655,742 A | 4/1987 | Vantard |
| 4,680,025 A | 7/1987 | Kruger et al. |
| 4,684,361 A | 8/1987 | Feldman et al. |
| 4,692,136 A | 9/1987 | Feldman et al. |
| 4,708,712 A | 11/1987 | Mulzet |
| 4,713,176 A | 12/1987 | Schoendorfer et al. |
| 4,734,089 A | 3/1988 | Cullis |
| 4,740,202 A | 4/1988 | Stacey et al. |
| 4,740,313 A | 4/1988 | Schoendorfer et al. |
| 4,755,300 A | 7/1988 | Fischel et al. |
| 4,767,396 A | 8/1988 | Powers |
| 4,795,419 A | 1/1989 | Yawn et al. |
| 4,795,448 A | 1/1989 | Stacey et al. |
| 4,806,247 A | 2/1989 | Schoendorfer et al. |
| 4,806,252 A | 2/1989 | Brown et al. |
| 4,808,307 A | 2/1989 | Fischel et al. |
| 4,850,995 A | 7/1989 | Tie et al. |
| 4,869,812 A | 9/1989 | Schoendorfer et al. |
| 4,871,462 A | 10/1989 | Fischel et al. |
| 4,876,013 A | 10/1989 | Shmidt et al. |
| 4,889,524 A | 12/1989 | Fell et al. |
| 4,911,833 A | 3/1990 | Schoendorfer et al. |
| 4,934,995 A | 6/1990 | Cullis |
| 4,940,543 A | 7/1990 | Brown et al. |
| 4,943,273 A | 7/1990 | Pages |
| 4,968,295 A | 11/1990 | Neumann |
| 4,983,156 A | 1/1991 | Knelson |
| 4,983,158 A | 1/1991 | Headley |
| 4,985,153 A | 1/1991 | Kuroda et al. |
| 4,994,188 A | 2/1991 | Prince |
| 5,039,401 A | 8/1991 | Columbus et al. |
| 5,045,048 A | 9/1991 | Kaleskas et al. |
| 5,098,372 A | 3/1992 | Jonsson |
| 5,098,373 A | 3/1992 | Polaschegg |
| 5,100,372 A | 3/1992 | Headley |
| 5,100,564 A | 3/1992 | Pall et al. |
| 5,112,298 A | 5/1992 | Prince et al. |
| 5,114,396 A | 5/1992 | Unger et al. |
| 5,135,667 A | 8/1992 | Schoendorfer |
| 5,141,486 A | 8/1992 | Antwiler |
| 5,147,290 A | 9/1992 | Jonsson |
| 5,154,716 A | 10/1992 | Bauman et al. |
| 5,174,894 A | 12/1992 | Ohsawa et al. |
| 5,194,145 A | 3/1993 | Schoendorfer |
| 5,217,426 A | 6/1993 | Bacehowski et al. |
| 5,217,427 A | 6/1993 | Cullis |
| 5,234,403 A | 8/1993 | Yoda et al. |
| 5,254,248 A | 10/1993 | Nakamura |
| 5,273,517 A | 12/1993 | Barone et al. |
| 5,277,701 A | 1/1994 | Christie et al. |
| 5,298,016 A | 3/1994 | Gordon |
| 5,298,171 A | 3/1994 | Biesel |
| 5,300,060 A | 4/1994 | Nelson |
| 5,316,540 A | 5/1994 | McMannis et al. |
| 5,318,511 A | 6/1994 | Riquier et al. |
| 5,318,512 A | 6/1994 | Neumann |
| 5,348,533 A | 9/1994 | Papillon et al. |
| 5,368,542 A | 11/1994 | McMannis et al. |
| 5,368,555 A | 11/1994 | Sussman et al. |
| 5,386,734 A | 2/1995 | Pusinelli |
| 5,387,174 A | 2/1995 | Rochat |
| 5,387,187 A | 2/1995 | Fell et al. |
| 5,403,272 A | 4/1995 | Deniega et al. |
| 5,405,308 A | 4/1995 | Headley et al. |
| 5,417,650 A | 5/1995 | Gordon |
| 5,431,814 A | 7/1995 | Jorgensen |
| 5,437,598 A | 8/1995 | Antwiler |
| 5,437,624 A | 8/1995 | Langley |
| 5,462,667 A | 10/1995 | Wollinsky et al. |
| 5,470,483 A | 11/1995 | Bene et al. |
| 5,484,396 A | 1/1996 | Naficy |
| 5,494,592 A | 2/1996 | Latham, Jr. et al. |
| 5,505,685 A | 4/1996 | Antwiler |
| 5,514,070 A | 5/1996 | Pages |
| 5,543,062 A | 8/1996 | Nishimura |
| 5,551,941 A | 9/1996 | Howell |
| 5,585,007 A | 12/1996 | Antanavich et al. |
| 5,607,579 A | 3/1997 | Latham, Jr. et al. |
| 5,649,903 A | 7/1997 | Deniega et al. |
| 5,651,766 A | 7/1997 | Kingsley et al. |
| 5,656,163 A | 8/1997 | Brown |
| 5,665,061 A | 9/1997 | Antwiler |
| 5,712,798 A | 1/1998 | Langley et al. |
| 5,728,060 A | 3/1998 | Kingsley et al. |
| 5,733,253 A | 3/1998 | Headley et al. |
| 5,733,446 A | 3/1998 | Holm |
| 5,733,545 A | 3/1998 | Hood, III |
| 5,738,792 A | 4/1998 | Schoendorfer |
| 5,762,791 A | 6/1998 | Deniega et al. |
| 5,779,660 A | 7/1998 | Kingsley et al. |
| 5,783,085 A | 7/1998 | Fischel |
| 5,792,351 A | 8/1998 | Wehrle et al. |
| 5,849,203 A | 12/1998 | Brown et al. |
| 5,882,289 A | 3/1999 | Sakota et al. |
| 5,906,589 A | 5/1999 | Gordon et al. |
| 5,919,125 A | 7/1999 | Berch |
| 5,964,724 A | 10/1999 | Rivera et al. |
| 5,970,432 A | 10/1999 | Ishimoto et al. |
| 5,980,760 A | 11/1999 | Min et al. |
| 6,007,725 A | 12/1999 | Brown |

(56) References Cited

U.S. PATENT DOCUMENTS

| | | |
|---|---|---|
| 6,059,979 A | 5/2000 | Brown |
| 6,207,063 B1 | 3/2001 | Brown |
| 6,234,989 B1 | 5/2001 | Brierton et al. |
| 6,296,602 B1 | 10/2001 | Headley |
| 6,464,624 B2 | 10/2002 | Pages |
| 6,497,676 B1 | 12/2002 | Childers et al. |
| 6,558,307 B2 | 5/2003 | Headley |
| 6,623,443 B1 | 9/2003 | Polaschegg |
| 6,743,192 B1 | 6/2004 | Sakota et al. |
| 7,115,205 B2 | 10/2006 | Robinson et al. |
| 7,186,231 B2 | 3/2007 | Takagi et al. |
| 7,270,645 B2 | 9/2007 | Langley et al. |
| 7,704,454 B1 | 4/2010 | Langley et al. |
| 8,628,489 B2 | 1/2014 | Pages et al. |
| 8,702,637 B2 | 4/2014 | Pages et al. |
| 8,759,094 B2 | 6/2014 | Ranby |
| 2001/0000185 A1 | 4/2001 | Keller et al. |
| 2001/0027156 A1 | 10/2001 | Egozy et al. |
| 2002/0043492 A1 | 4/2002 | Bischof |
| 2002/0062100 A1 | 5/2002 | Pierce et al. |
| 2002/0120227 A1 | 8/2002 | Childers et al. |
| 2003/0055375 A1 | 3/2003 | Holst et al. |
| 2003/0066807 A1 | 4/2003 | Suzuki |
| 2003/0125881 A1 | 7/2003 | Ryan |
| 2003/0175150 A1 | 9/2003 | Grimm |
| 2004/0186409 A1 | 9/2004 | Cavalcanti et al. |
| 2005/0209522 A1 | 9/2005 | Tadokoro et al. |
| 2005/0235733 A1 | 10/2005 | Holst et al. |
| 2006/0058167 A1 | 3/2006 | Ragusa et al. |
| 2006/0155236 A1 | 7/2006 | Gara et al. |
| 2007/0112289 A1 | 5/2007 | Cavalcanti et al. |
| 2008/0146993 A1 | 6/2008 | Krishna |
| 2012/0175313 A1 | 7/2012 | Barry, Jr. et al. |
| 2014/0039373 A1 | 2/2014 | Ragusa et al. |
| 2014/0356851 A1 | 12/2014 | Pages et al. |
| 2018/0344921 A1 | 12/2018 | Ragusa |

FOREIGN PATENT DOCUMENTS

| | | |
|---|---|---|
| EP | 0171749 A1 | 2/1986 |
| EP | 0208061 A1 | 1/1987 |
| EP | 257755 A1 | 3/1988 |
| EP | 0578086 A1 | 1/1994 |
| EP | 619145 A2 | 10/1994 |
| EP | 0654277 A1 | 5/1995 |
| EP | 664159 A1 | 7/1995 |
| EP | 799645 A1 | 10/1997 |
| EP | 0885619 A1 | 12/1998 |
| EP | 1057534 A1 | 12/2000 |
| EP | 1295619 A2 | 3/2003 |
| EP | 1374927 A1 | 1/2004 |
| FR | 2258898 A1 | 8/1975 |
| GB | 2047110 A | 11/1980 |
| JP | S59-066952 | 1/1984 |
| JP | S59-069166 | 4/1984 |
| JP | H02-052665 | 2/1990 |
| JP | H03-131268 | 6/1991 |
| JP | H07-075746 | 3/1995 |
| JP | H08-131539 | 5/1996 |
| JP | H09-192215 | 7/1997 |
| JP | 2002-291872 A | 10/2002 |
| JP | 2008-506424 A | 3/2008 |
| SU | 660718 A1 | 5/1979 |
| SU | 762982 A1 | 9/1980 |
| SU | 1146098 A1 | 3/1985 |
| WO | WO-1985/02561 A1 | 6/1985 |
| WO | WO-1990/00059 A1 | 1/1990 |
| WO | WO-1990/07383 A1 | 7/1990 |
| WO | WO-1994/06535 A1 | 3/1994 |
| WO | WO-1996/11747 A2 | 4/1996 |
| WO | WO-1996/33023 A1 | 10/1996 |
| WO | WO-2002/05059 A2 | 1/2002 |
| WO | WO-2007/041716 A1 | 4/2007 |

OTHER PUBLICATIONS

Lemmens et al., Estimating blood volume in obese and morbidly obese patients. Obes Surg. Jun. 2006;16(6):773-6.

Nadler et al., Prediction of blood volume in normal human adults. Surgery. Feb. 1962;51(2):224-32.

Winters, Complications of donor apheresis. J Clin Apher. Jul. 2006;21(2):132-41.

International Search Report and Written Opinion for Application No. PCT/US2018/033826, dated Aug. 3, 2018, 10 pages.

SYSTEM AND METHOD FOR COLLECTING PLASMA

TECHNICAL FIELD

The present invention relates to systems and methods for blood apheresis, and more particularly system and methods for collecting a plasma product.

BACKGROUND ART

Apheresis is a procedure in which individual blood components can be separated and collected from whole blood temporarily withdrawn from a subject. Typically, whole blood is withdrawn through a needle inserted into a vein of the subjects arm and into a cell separator, such as a centrifugal bowl. Once the whole blood is separated into its various components, one or more of the components (e.g., plasma) can be removed from the centrifugal bowl. The remaining components can be returned to the subject along with optional compensation fluid to make up for the volume of the removed component. The process of drawing and returning continues until the quantity of the desired component has been collected, at which point the process is stopped. A central feature of apheresis systems is that the processed but unwanted components are returned to the donor. Separated blood components may include, for example, a high density component such as red blood cells, an intermediate density component such as platelets or white blood cells, and a lower density component such as plasma.

Many jurisdictions have regulations regarding the amount of whole blood and/or blood components that can be removed from a donor. For example, the U.S. Food and Drug Administration ("the FDA") sets both an upper limit on the volume of plasma that may be collected (e.g., 800 ml for an adult weighing more than 175 pounds) as well as an upper limit on the total collection volume (e.g., 880 ml for an adult weighing more than 175 pounds). Prior art plasma collection systems are unable to determine the total volume of plasma that has been collected (e.g., because the product collected is a mixture of plasma and anticoagulant) and, therefore collect based on the total collection volume, even if the total volume of plasma that has been collected is below the limit prescribed by the FDA.

SUMMARY OF THE INVENTION

In accordance with some embodiments of the present invention, a method for collecting plasma includes determining the weight and hematocrit of a donor, and inserting a venous-access device into the donor. Once the venous access device is inserted, the method may withdraw whole blood from the donor through the venous-access device and a draw line that is connected to a blood component separation device. The method may then introduce anticoagulant into the withdrawn whole blood through an anticoagulant line and separate, using the blood component separation device, the withdrawn whole blood into a plasma component and at least a second blood component. Once separated, the plasma component may be collected from the blood component separation device and into a plasma collection container. During processing, the method may calculate (1) a percentage of anticoagulant in the collected plasma component, and (2) a volume of pure plasma collected within the plasma collection container. The volume of pure plasma may be based, at least in part, on the calculated percentage of anticoagulant in the collected plasma component. The method may continue the process (e.g., withdrawing whole blood, introducing anticoagulant into the whole blood, separating the blood, collecting the plasma, and calculating the percentage of anticoagulant and volume of pure plasma) until a target volume of pure plasma is collected within the plasma collection container.

In some embodiments, the method may determine a change in volume within an anticoagulant container, and the calculated percentage of anticoagulant in the collected plasma may be based, at least in part, on the change in volume within the anticoagulant container. Additionally or alternatively, the method may determine a volume of anticoagulant introduced into the whole blood based on a number of rotations of an anticoagulant pump. In such embodiments, the calculated percentage of anticoagulant in the collected plasma may be based, at least in part, on the number of rotations of the anticoagulant pump. The method may also determine a volume of anticoagulant within the blood component separation device, and the calculated percentage of anticoagulant in the collected plasma may be based, at least in part, on the volume of anticoagulant within the blood component separation device.

In further embodiments, the method may monitor the volume and/or weight of the plasma component collected within the plasma collection container (e.g., using a weight sensor), and the calculated volume of pure plasma collected within the plasma collection device may be based, at least in part, on the monitored volume and/or weight of the collected plasma component. Additionally or alternatively, determining the hematocrit of the donor may include monitoring a volume of red blood cells collection within the blood separation device. In such embodiments, the determined hematocrit of the donor may be based, at least in part, on the monitored volume of red blood cells collected within the blood separation device and the volume of whole blood withdrawn from the donor.

The target volume of pure plasma may be based, at least in part, on the weight of the donor. The percentage of anticoagulant in the collected plasma component may include at least a portion of the anticoagulant introduced into the withdrawn blood and at least a portion of a volume of anticoagulant that is added to the system during a priming step. After collecting at least a portion of the target volume of pure plasma, the method may return the second blood component to the donor through a return line.

In accordance with additional embodiments, a system for collecting plasma includes a venous-access device for drawing whole blood from a subject and returning blood components to the subject, and a blood component separation device for separating the drawn blood into a plasma component and a second blood component. The blood component separation device has an outlet and is configured to send the plasma component to a plasma container. The system may also include a blood draw line fluidly connected to the venous-access device and an anticoagulant line connected to an anticoagulant source. The blood draw line transports drawn whole blood to the blood component separation device, and the flow through the blood draw line may be controlled by a blood draw pump. The anticoagulant line may introduce anticoagulant into the drawn whole blood.

Additionally, the system may include a controller that controls the operation of the centrifuge bowl. The controller may also calculate (1) a percentage of anticoagulant in the collected plasma component, and (2) a volume of pure plasma collected within the plasma container. The volume of pure plasma may be based, at least in part, upon the percentage of anticoagulant in the collected plasma component. The controller may stop the blood draw pump when a target volume of pure plasma (e.g., based, at least in part, on the weight of the donor) is collected within the plasma container. In some embodiments, the percentage of anticoagulant in the collected plasma component may be based, at least in part, on the volume of anticoagulant added to the drawn whole blood and the subject's hematocrit.

The system may also include an anticoagulant source weight sensor that measures the weight of the anticoagulant source. The controller may monitor the change in volume within the anticoagulant container based on the measured weight of the anticoagulant source, and the calculated percentage of anticoagulant in the collected plasma may be based, at least in part, on the change in volume within the anticoagulant source. Additionally or alternatively, the controller may monitor the number of rotations of an anticoagulant pump to determine a volume of anticoagulant introduced into the whole blood. In such embodiments, the calculated percentage of anticoagulant in the collected plasma may be based, at least in part, on the number of rotations of the anticoagulant pump.

In some embodiments, the system may include an optical sensor located on the blood component separation device. The optical sensor may monitor the contents of the blood component separation device and determine if a volume of anticoagulant remains within the blood component separation device. The calculated percentage of anticoagulant in the collected plasma may be based, at least in part, on the volume of anticoagulant within the blood component separation device.

In additional embodiments, the system may also include a plasma container weight sensor that monitors a volume and/or weight of the plasma component collected within the plasma collection container. The calculated volume of pure plasma collected within the plasma collection container may be based, at least in part, on the monitored volume and/or weight of collected plasma component. The system may also have an optical sensor located on the blood component separation device. The optical sensor may monitor the volume of red blood cells collected within the blood separation device. The controller may then determine the subject's hematocrit based, at least in part, upon on the monitored volume of red blood cells collected within the blood separation device and the volume of whole blood withdrawn from the donor. The percentage of anticoagulant in the collected plasma component may include at least a portion of the anticoagulant introduced into the withdrawn blood and at least a portion of a volume of anticoagulant added to the system during a priming step.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Illustrative embodiments of the present invention provide blood processing systems and methods for collecting a target volume of pure plasma. The system and method calculate a percentage of anticoagulant collected within a plasma collection container (e.g., in addition to the plasma that is collected within the container) based on the amount of anticoagulant added to the system and the hematocrit of the donor. The system/method may then calculate the volume of pure plasma (e.g., plasma without anticoagulant) that has been collected within the container. Details of the illustrative embodiments are discussed below.

Figure 1:
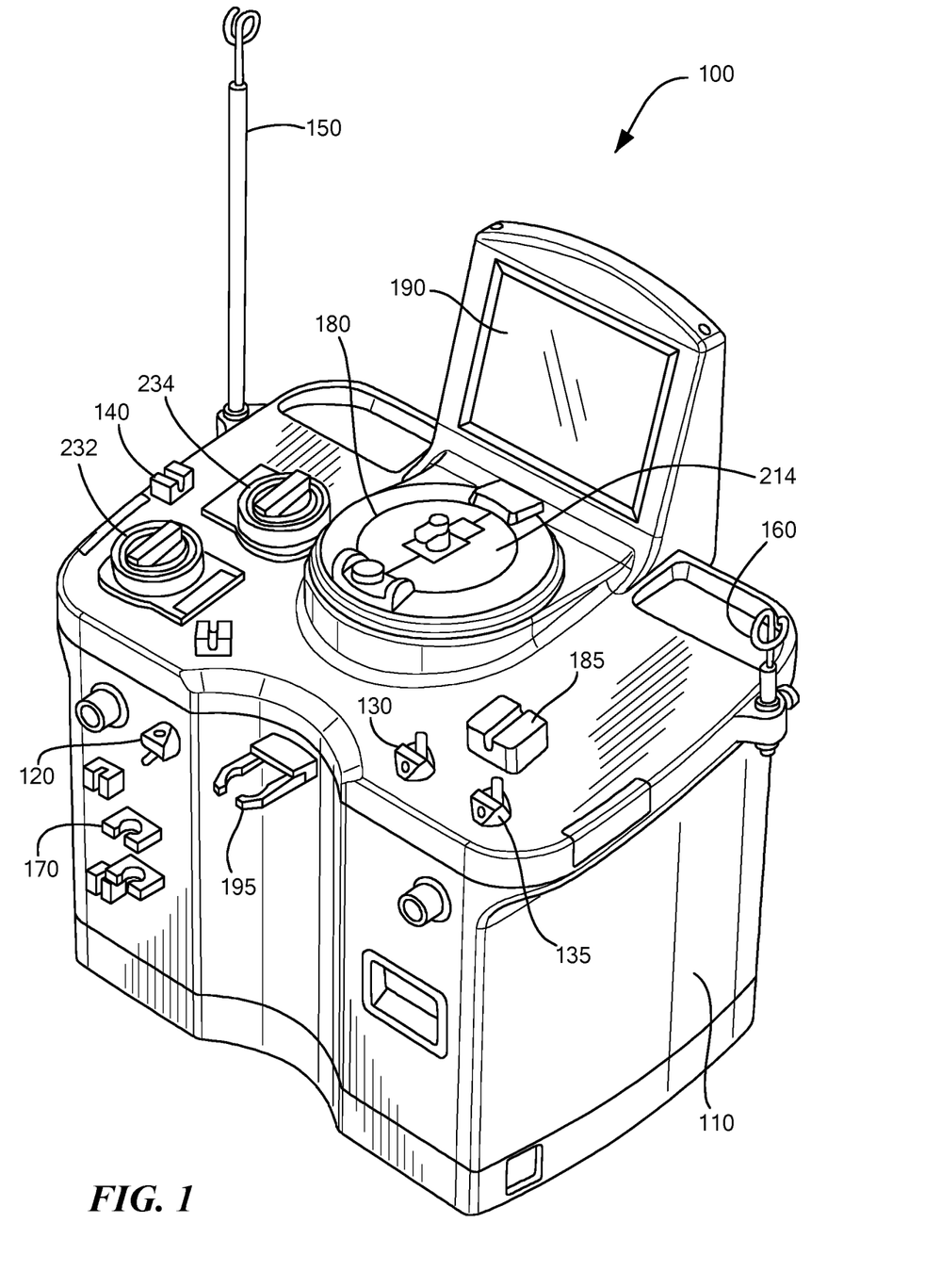
FIG. 1 schematically shows a perspective view of a blood processing system in accordance with some embodiments of the present invention.
Figure 2:
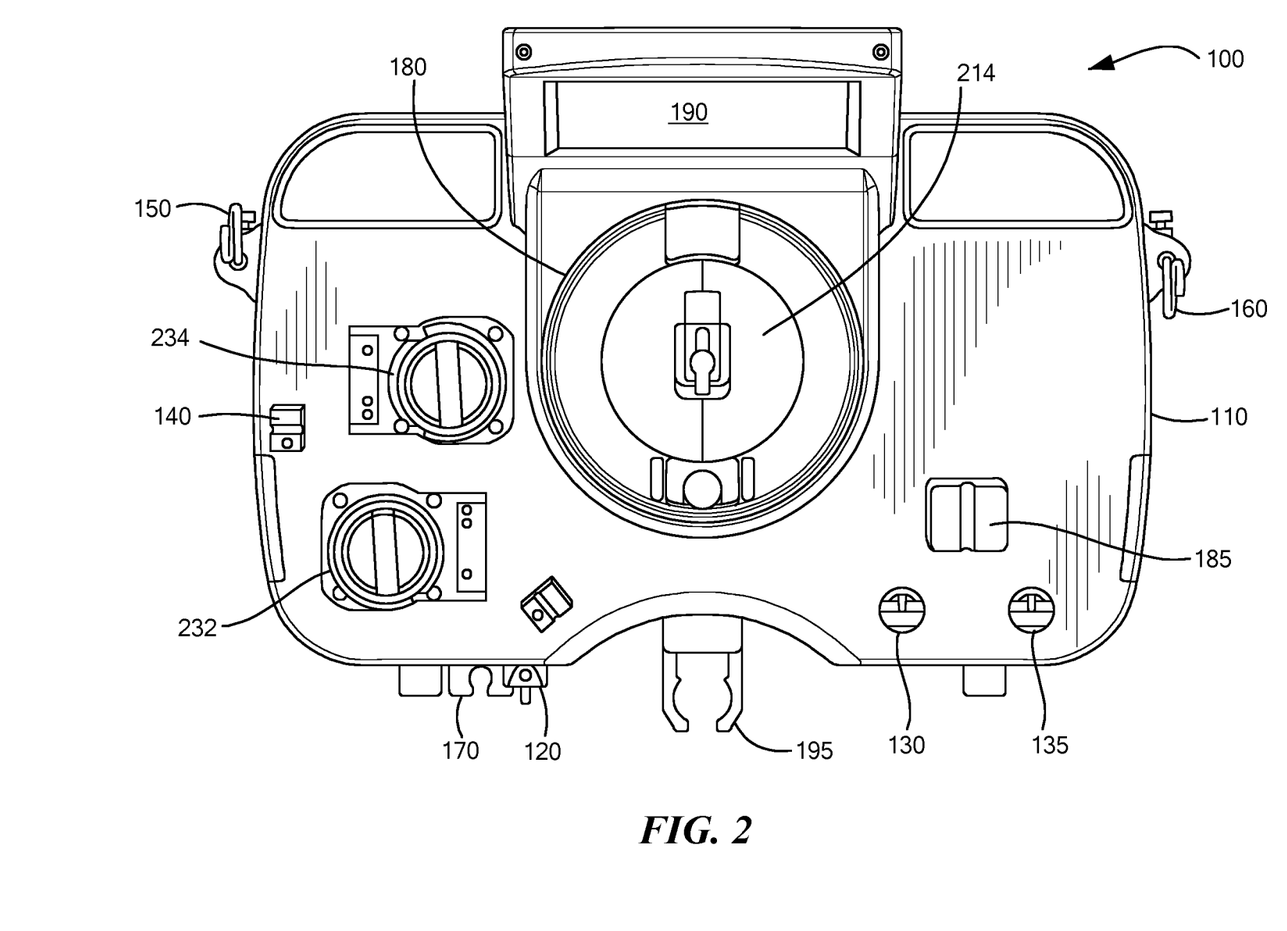
FIG. 2 schematically shows a top view of the blood processing system of FIG. 1, in accordance with some embodiments of the present invention.

As shown in FIGS. 1 and 2, the blood processing system 100 includes a cabinet 110 that houses the main components of the system 100 (e.g., the non-disposable components). Within the cabinet 110, the system 100 may include a first/blood pump 232 that draws whole blood from a subject, and a second/anticoagulant pump 234 that pumps anticoagulant through the system 100 and into the drawn whole blood. Additionally, the system 100 may include a number of valves that may be opened and/or closed to control the fluid flow through the system 100. For example, the system 100 may include a donor valve 120 that may open and close to selectively prevent and allow fluid flow through a donor line 218 (e.g., an inlet line; FIG. 3), and a plasma valve 130 that selectively prevents and allows fluid flow through an outlet/plasma line 222 (FIG. 3). Some embodiments may also include a saline valve 135 that selectively prevents and allows saline to flow through a saline line 223.

To facilitate the connection and installation of a disposable set and to support the corresponding fluid containers, the system 100 may include an anticoagulant pole 150 on which the anticoagulant solution container 210 (FIG. 3) may be hung, and a saline pole 160 on which a saline solution container 217 (FIG. 3) may be hung (e.g., if the procedure being performed requires the use of saline). Additionally, in some applications, it may be necessary and/or desirable to filter the whole blood drawn from the subject for processing. To that end, the system 100 may include blood filter holder 170 in which the blood filter (located on the disposable set) may be placed.

As discussed in greater detail below, apheresis systems 100 in accordance with embodiments of the present invention withdraw whole blood from a subject through a venous access device 206 (FIG. 3) using the blood pump 232. As the system 100 withdraws the whole blood from the subject, the whole blood enters a blood component separation device 214, such as a Latham type centrifuge (other type of separation chambers and devices may be used, such as, without limitation, an integral blow-molded centrifuge bowl, as described in U.S. Pat. Nos. 4,983,158 and 4,943,273, which are hereby incorporated by reference). The blood component separation device 214 separates the whole blood into its constituent components (e.g., red blood cells, white blood cell, plasma, and platelets). Accordingly, to facilitate operation of the separation device 214, the system 100 may also include a well 180 in which the separation device 214 may be placed and in which the separation device 214 rotates (e.g., to generate the centrifugal forces required to separate the whole blood).

To allow the user/technician to monitor the system operation and control/set the various parameters of the procedure, the system 100 may include a user interface 190 (e.g., a touch screen device) that displays the operation parameters, any alarm messages, and buttons which the user/technician may depress to control the various parameters. Additional components of the blood processing system 100 are discussed in greater detail below (e.g., in relation to the system operation).

Figure 3:
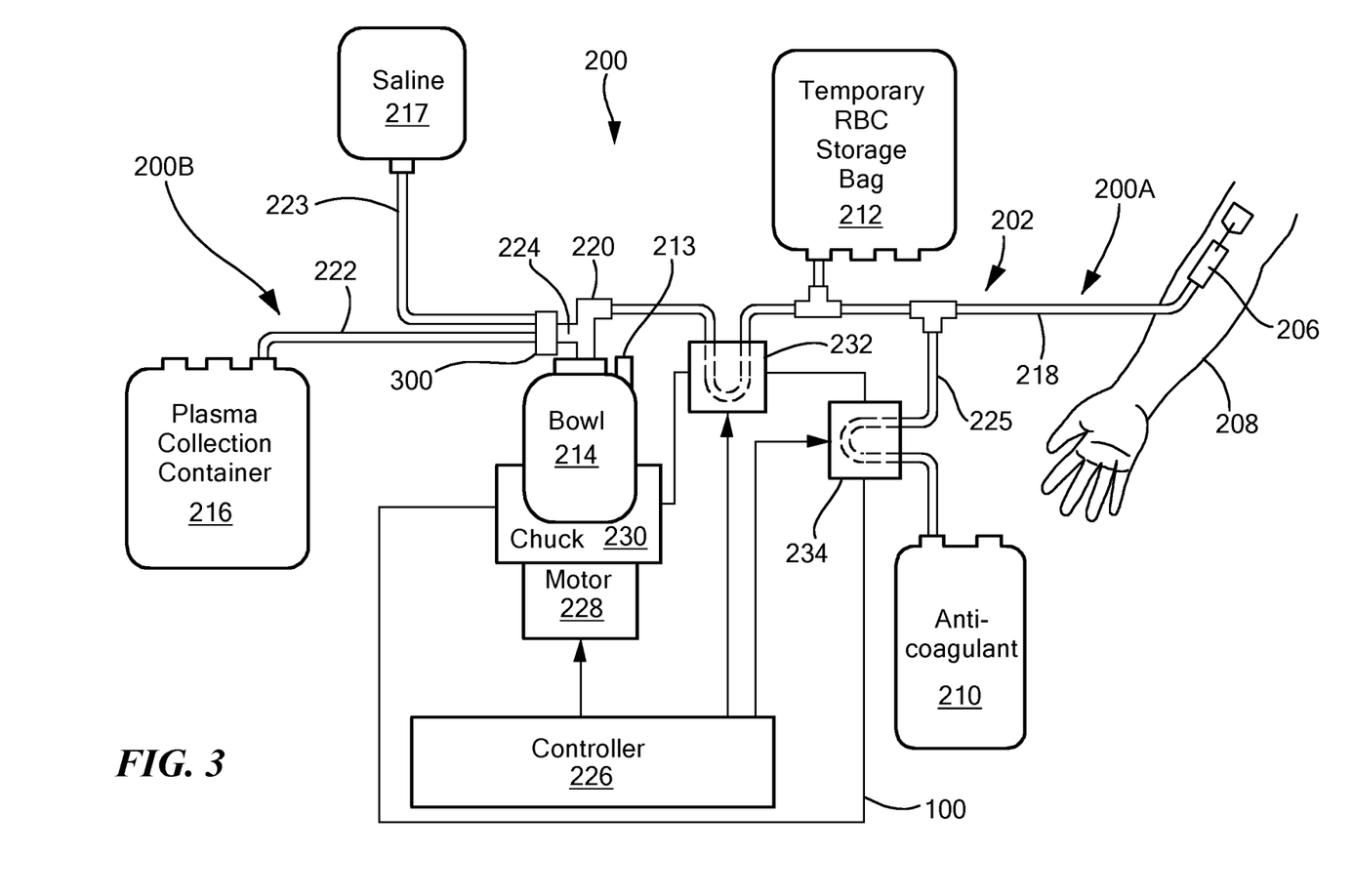
FIG. 3 schematically shows a disposable set installed within the blood processing system of FIG. 1, in accordance with some embodiments of the present invention.

FIG. 3 is a schematic block diagram of the blood processing system 100 and a disposable collection set 200 (with an inlet disposable set 200A and an outlet disposable set 200B) that may be loaded onto/into the blood processing system 100, in accordance with the present invention. The collection set 200 includes a venous access device 206 (e.g., a phlebotomy needle) for withdrawing blood from a donor's arm 208, a container of anti-coagulant 210, a centrifugation bowl 214 (e.g., a blood component separation device), a saline container 217, and a final plasma collection bag 216. The blood/inlet line 218 couples the venous access device 206 to an inlet port 220 of the bowl 214, the plasma/outlet line 222 couples an outlet port 224 of the bowl 214 to the plasma collection bag 216, and a saline line 223 connects the outlet port 224 of the bowl 214 to the saline container 217. An anticoagulant line 225 connects the anti-coagulant container 210 to the inlet line 218. In addition to the components mentioned above and as shown in FIG. 3, the blood processing system 100 includes a controller 226, a motor 228, and a centrifuge chuck 230. The controller 226 is operably coupled to the two pumps 232 and 234, and to the motor 228, which, in turn, drives the chuck 230. The controller 226 may be operably coupled to and in communication with the user interface 190.

In operation, the disposable collection set 200 (e.g., the inlet disposable set 200A and the outlet disposable set 200B) may be loaded onto/into the blood processing system 100 prior to blood processing. In particular, the blood/inlet line 218 is routed through the blood/first pump 232 and the anticoagulant line 225 from the anti-coagulant container 210 is routed through the anticoagulant/second pump 234. The centrifugation bowl 214 may then be securely loaded into the chuck 230. Once the bowl 214 is secured in place, the technician may install the outlet disposable set 200B. For example the technician may connect a bowl connector 300 to the outlet 224 of the bowl 214, install the plasma container 216 into the weight senor 195, run the saline line 223 through valve 135, and run the plasma/outlet line 222 through valve 130 and the line sensor 185. Once the disposable set 200 is installed and the anticoagulant and saline containers 210/217 are connected, the system 100 is ready to begin blood processing.

Figure 4:
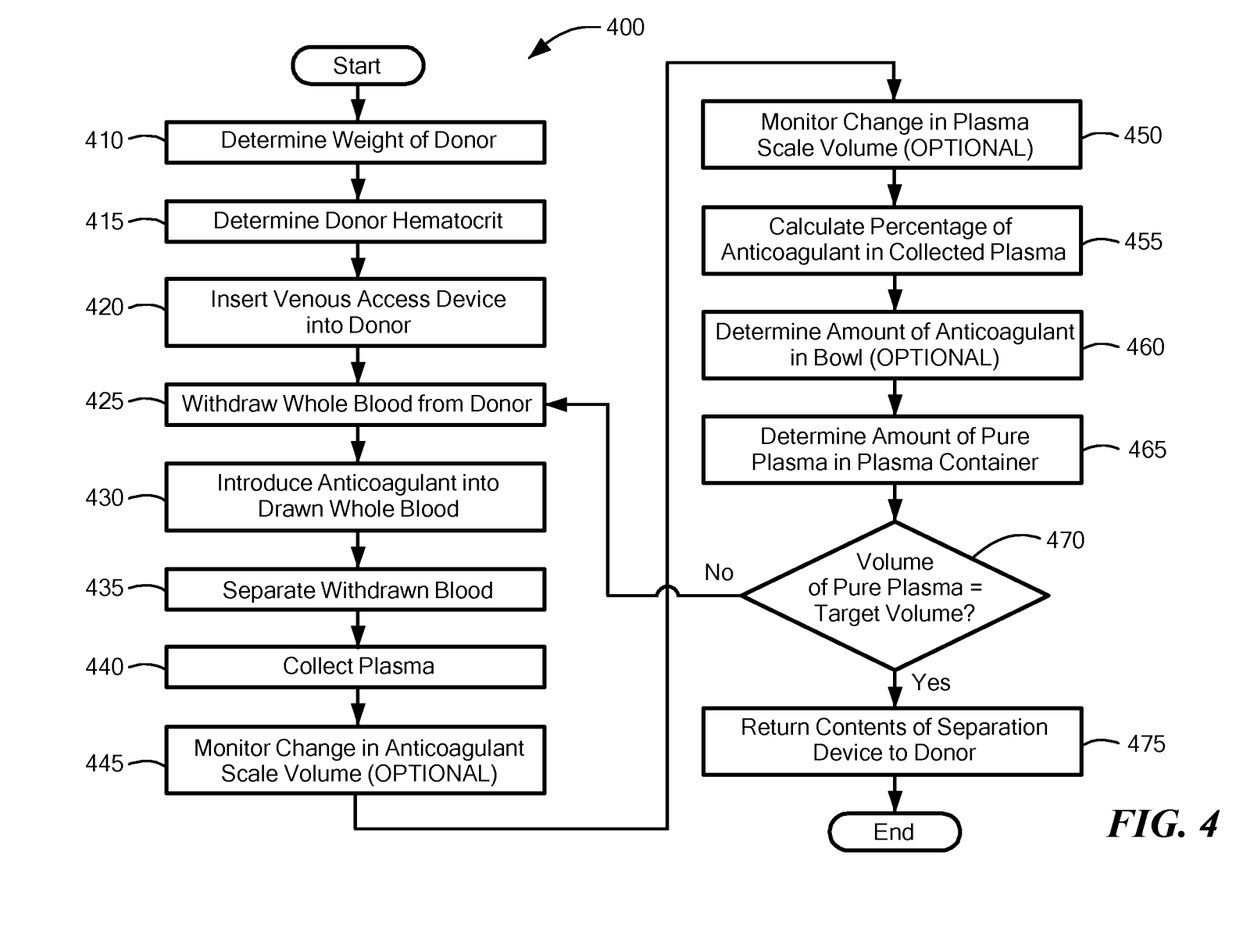
FIG. 4 is a flowchart depicting a method of collecting plasma, in accordance with embodiments of the present invention.

FIG. 4 is a flowchart depicting an exemplary method of collecting plasma in accordance with various embodiments of the present invention. Prior to connecting the donor to the blood processing device 100, it is beneficial (and perhaps necessary in some instances) to obtain/determine some information regarding the donor, namely, the donor's weight (Step 410) and hematocrit (Step 415). Not only does this information help determine if the individual is a viable donor and the volumes of blood components that may be withdrawn/collected (e.g., per the FDA guidelines), the hematocrit may be used during processing to help collect a target volume of plasma. The technician may obtain/determine the donor's weight by weighing the donor (e.g., on a scale). To obtain/determine the donor's hematocrit, the technician may draw a blood sample from the donor and test the sample of blood. Additionally or alternatively, as discussed in greater detail below, the system may determine the hematocrit during blood processing. For example, the blood processing device 100 may include a hematocrit sensor (not shown) that determines the hematocrit of the blood flowing into the blood processing device 100 and/or the system 100 may determine the hematocrit based on a volume of red blood cells collected within the bowl 214.

Once the lines 222/223 are in place and the technician has determined the donor's weight and/or hematocrit (if needed), the user/technician may insert the venous access device 206 into the donor's arm 208 (Step 420). Next, the controller 226 activates the two pumps 232, 234 and the motor 228. Operation of the two pumps 232, 234 causes whole blood to be drawn from the donor (step 425), anticoagulant from container 210 to be introduced into the drawn whole blood (step 430), and the now anticoagulated whole blood to be delivered to the inlet port 220 of the bowl 214.

It should be noted that the anticoagulant line 225 may also include a bacteria filter (not shown) that prevents any bacteria in the anticoagulant source 210, the anticoagulant, or the anticoagulant line 225 from entering the system 100 and/or the subject. Additionally, the anticoagulant line 225 may include an air detector 140 that detects the presence of air within the anticoagulant. The presence of air bubbles within any of the system 100 lines can be problematic for the operation the system 100 and may also be harmful to the subject if the air bubbles enter the blood stream. Therefore, the air detector may be connected to an interlock that stops the flow within the anticoagulant line 225 in the event that an air bubble is detected (e.g., by stopping the anticoagulant pump 234), thereby preventing the air bubbles from entering the subject.

As the anti-coagulated whole blood is withdrawn from the subject and contained within the blood component separation device 214, the blood component separation device 214 separates the whole blood into several blood components (Step 435). For example, the blood component separation device 214 may separate the whole blood into a first, second, third, and, perhaps, fourth blood component. More specifically, the blood component separation device 214 (and the centrifugal forces created by rotation of the separation device 214) can separate the whole blood into plasma, platelets, red blood cells ("RBC"), and, perhaps, white blood cells ("WBC"). The higher density component, i.e., RBC, is forced to the outer wall of the bowl 214 while the lower density plasma lies nearer the core. A buffy coat is formed between the plasma and the RBC. The buffy coat is made up of an inner layer of platelets, a transitional layer of platelets and WBC and an outer layer of WBC. The plasma is the component closest to the outlet port and is the first fluid component displaced from the bowl 214 via the outlet port 224 as additional anticoagulated whole blood enters the bowl 214 through the inlet port 220.

As shown in FIG. 3, the system 100 may also include an optical sensor 213 that may be applied to a shoulder portion of the bowl 214. The optical sensor monitors each layer of the blood components as they gradually and coaxially advance toward the core from the outer wall of the bowl 214. The optical sensor 213 may be mounted in a position (e.g., within the well 180) at which it can detect the buffy coat and/or the red blood cells reaching a particular radius, and the steps of drawing the whole blood from the subject/donor and introducing the whole blood into the bowl 12 may be altered and/or terminated in response to the detection.

Additionally, in some embodiments, the optical sensor 213 may be used to determine the hematocrit of the donor during processing. For example, as the bowl 214 fills with red blood cells and the optical sensor 213 detects the layer of red blood cells, the system 100 (e.g., the controller) can determine the volume of red blood cells within bowl 214 based on the location of the red blood cell layer and the fixed/known bowl volume. The system 100 may then calcuate the donor hematocrit based on the volume of red blood cells within the bowl and the volume of whole blood that has been processed to that point.

Once the blood component separation device 214 has separated the blood into the various components, one or more of the components can be removed from the blood component separation device 214. For instance, the plasma may be removed to a plasma container 216 (e.g., a plasma bottle) through line 222 (Step 440). As noted above, some embodiments of the system 100 may include a weight sensor 195 (FIG. 1) that measures the amount of plasma collected. The plasma collection process may continue until the a target volume of pure plasma (discussed in greater detail below) is collected within the plasma collection container 216. Although not shown, if the blood processing system 100 and/or the disposable set 200 include platelet, red blood cell, and/or white blood cell bags, each of the bags/containers may include similar weight sensors (e.g., load cells).

In some embodiments, the system 100 may also include a line sensor 185 (mentioned above) that can determine the type of fluid (e.g., plasma, platelets, red blood cells etc.) exiting the blood component separation device 214. In particular, the line sensor 185 consists of an LED which emits light through the blood components leaving the bowl 214 and a photo detector which receives the light after it passes through the components. The amount of light received by the photo detector is correlated to the density of the fluid passing through the line. For example, if plasma is exiting the bowl 214, the line sensor 185 will be able to detect when the plasma exiting the bowl 214 becomes cloudy with platelets (e.g., the fluid existing the bowl 214 is changing from plasma to platelets). The system 100 may then use this information to either stop the removal of blood components from the bowl 214, stop drawing whole blood from the subject, or redirect the flow by, for example, closing one valve an opening another.

It is important to note that during processing, the osmolarity of the red blood cells prevents the anticoagulant introduced into the whole blood from entering/remaining with the red blood cells (e.g., within the bowl 214). Rather, the anticoagulant mixes with the plasma component. Therefore, the anticoagulant exits the bowl 214 with the plasma and is collected within collection container 216 along with the plasma. In other words, the weight of the product measured by the weight sensor 195 is the weight of the plasma, as well as any anticoagulant that is mixed with the plasma—the weight provided by the weight sensor 195 is not the weight of pure plasma.

Additionally, whole blood contains a variable amount of plasma, as determined by the donor's hematocrit. The hematocrit for typical donors can vary from 38% to 54%, which means that for 100 ml of whole blood, the volume of plasma can vary from 36 to 62 ml. Furthermore, the amount of anticoagulant added to the withdrawn whole blood is fixed (e.g., it does not depend on the hematocrit of the donor), meaning that the percentage of anticoagulant in the collected plasma may vary from 9.7% to 12.7% for donor hematocrits between 38% to 54%, respectively. Therefore, not only does the volume measured by the weight sensor 195 include the volume of anticoagulant, that volume of anticoagulant may vary from donor to donor based on the hematocrit.

As mentioned above, some embodiments of the present invention continue the blood processing/separation procedure until a target volume of pure plasma (e.g., plasma only—without the volume of any anticoagulant mixed with the plasma included in the target volume) is collected within the plasma collection container 216. To that end, some embodiments of the present invention may calculate the volume of pure plasma within the plasma collection container 216. For example, the technician or the system 100 (e.g., the controller) may calculate the percentage of anticoagulant within the collected plasma (Step 455) (e.g., the plasma contained within the plasma collection container 216) based on the amount of anticoagulant added/metered into the whole blood and the hematocrit of the donor. The technician and/or system can calculate the percentage of anticoagulant according to the following equation, where AC is the amount of anticoagulant added to the system 100. As noted above, because the osmolarity of the red blood cells prevents the anticoagulant from mixing with it, essentially all of the anticoagulant exits the bowl 214 and is collected within the plasma collection container 216 along with the plasma.

$$\% \, AC = \frac{1}{1 + (AC - 1)(1 - Hct_D)}$$

The amount of anticoagulant that is added to the system 100 can be determined in a number of ways. For example, the system 100 can base the amount of anticoagulant (e.g., the value of "AC" in the above equation) on the predetermined ratio of anticoagulant per unit of anticoagulated whole blood. In some embodiments, the value of "AC" may be the inverse of the predetermined ratio (e.g., "AC" would be 16 if the ratio of anticoagulant to anticoagulated whole blood was 1:16). Additionally or alternatively, the technician/system 100 can monitor the volume of anticoagulant added to the system. In such embodiments, the technician/system can monitor the volume of anticoagulant added to the system 100 based on the number of rotations of the anticoagulant pump (e.g., each rotation of the anticoagulant pump introduces a set volume of anticoagulant into the system 100) and/or based on the change in weight of the anticoagulant container 210 as measured by a weight sensor (discussed in greater detail below).

Once the technician/system 100 has calculated the percentage of anticoagulant within the plasma collection container 216, the technician/system 100 may then use this information to calculate the volume of pure plasma within the plasma collection container 216 (Step 465). For example, the technician/system 100 may determine the volume of anticoagulant within the container (based on the percentage of anticoagulant within the container 216) and subtract this volume from the total volume of fluid within the container 216 as measured by the weight sensor 195. The system 100 may continue to monitor the volume of pure plasma collected within the container 216 and continue processing whole blood (e.g., continue performing Steps 425, 430, 435, 440, 455, 460 and 465) until a target volume of pure plasma is collected within the plasma collection container 216 (Step 470) (e.g., 800 mL for an adult donor weighing more than 175 pounds or other limit prescribed by the FDA or similar governing body).

Once the system 100 has collected the target volume of pure plasma within the plasma collection container 216, the system 100 can return the remaining components (e.g., the components remaining within the bowl 214) to the subject (Step 475). For example, when all the plasma has been removed and the bowl 214 is full of RBCs (and any other blood component not collected), the controller 226 stops the draw of whole blood from the subject and reverses the direction of the blood/first pump 232 to draw the RBCs (and other components) from the bowl 214 directly back to the subject. Alternatively, if the system 100 is so equipped, the system may return the components to the subject via a dedicated return line.

In addition to the non-collected blood components (e.g., the components remaining in the bowl 214), the system 100 may also return saline to the patient/subject. The saline may be used as a compensation fluid to make up for the volume of the blood component (e.g., plasma) that was removed and collected, and is not being returned to the patient. To that end, during the return step (e.g., Step 475), the saline valve 135 may be opened to allow saline from the saline container 217 to flow through the saline line 223 and into the howl 214 (via outlet 224), where it can be returned to the patient/donor with or after the remaining blood components.

It should be noted that some embodiments may perform some additional and optional steps to help determine the volume of pure plasma within the plasma collection container 216. For example, as mentioned above, some embodiments may monitor the change in weight of the anticoagulant container 210 (e.g., as measured by a weight sensor/load cell on the anticoagulant container 210) (step 445). This measurement provides an indication of the volume of anticoagulant that has been added to the system 100, and may be used help determine the percentage of anticoagulant within the plasma collection container 216. Additionally or alternatively, some embodiments may similarly, monitor the change in weight and/or volume of the plasma and anticoagulant collected within the plasma collection container 216 (e.g., via weight sensor 195) (step 450). This measurement may be used to calculate of the total volume of pure plasma collected within the plasma collection container 216 (e.g., to obtain the total weight from which to subtract the calculated volume of anticoagulant).

Some embodiments may also (optionally) monitor the volume of anticoagulant remaining in the bowl 214 (step 460) (e.g., anticoagulant that did not mix with the plasma and/or otherwise remained in the bowl). For example, the system 100 may utilize the optical sensor on the bowl 214 to determine whether any anticoagulant remains within the bowl 214. If it does, the method 400/system 100 may modify the calculation of the amount of pure plasma collected within the plasma collection container (e.g., either increase the calculated amount or decreased the calculated amount), based on the volume of anticoagulant remaining within the bowl 214.

Various embodiment of the present invention provide numerous benefits over prior art plasma collection systems. In particular, as noted above, prior art plasmapheresis devices end plasma collection based on a total volume of anticoagulated plasma (e.g., pure plasma plus the added anticoagulant). Although this is the easiest method because it requires only that the product collection container be weighed, the amount of true product—the pure plasma—is dependent on the donor's hematocrit. In other words, prior art systems will collect more plasma from low hematocrit donors than from high hematocrit donors because of the variation of the percentage of anticoagulant in the product. Various embodiments of the present invention address the issues of prior art systems by collecting a standard volume (e.g., a target volume) of pure plasma from each donor. As noted above, embodiments of the present invention accomplish this by using knowledge of the donor's hematocrit and the amount of anticoagulant collected within the plasma collection container 216 (e.g., by counting pump rotations and/or using scale/weight sensors, etc.) to determine the percentage of anticoagulant in the product. Additionally, by stopping the plasma collection process based on a volume of pure plasma collected, embodiments of the present invention are able to collect a greater volume of plasma as compared to prior art systems that stop based on a plasma/anticoagulant mixture.

It is also important to note that, although the various embodiments discussed above are in relation to a blood processing system that collects plasma, the features discussed herein may be applied to any type of blood processing system. For example, the features described herein may be implemented on blood processing systems that collect and/or process red blood cells, platelets and/or white blood cells.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for collecting plasma comprising:
    (a) determining a weight of a donor;
    (b) determining a hematocrit of the donor;
    (c) inserting a venous-access device into the donor;
    (d) withdrawing whole blood from the donor through the venous-access device and a draw line, the draw line connected to a blood component separation device;
    (e) introducing anticoagulant into the withdrawn whole blood through an anticoagulant line;
    (f) separating the withdrawn whole blood into a plasma component and at least a second blood component using the blood component separation device;
    (g) collecting the plasma component from the blood component separation device and into a plasma collection container;
    (h) calculating a volume of anticoagulant in the collected plasma component as the plasma component is being collected in the plasma collection container;
    (i) calculating a volume of pure plasma collected within the plasma collection container based, at least in part, on the calculated volume of anticoagulant in the collected plasma component; and
    (j) continuing steps (d) through (i) until a target volume of pure plasma is collected within the plasma collection container.

2. A method according to claim 1, further comprising:
    determining a change in volume within an anticoagulant container, the calculated volume of anticoagulant in the collected plasma component being based, at least in part, on the change in volume within the anticoagulant container.

3. A method according to claim 1, further comprising:
    determining a volume of anticoagulant introduced into the whole blood based on a number of rotations of an anticoagulant pump, the calculated volume of anticoagulant in the collected plasma component being based, at least in part, on the number of rotations of the anticoagulant pump.

4. A method according to claim 1, further comprising:
    determining a volume of anticoagulant within the blood component separation device, the calculated volume of anticoagulant in the collected plasma component being based, at least in part, on the volume of anticoagulant within the blood component separation device.

5. A method according to claim 1, further comprising: monitoring a volume of plasma component collected within the plasma collection container, the calculated volume of pure plasma collected within the plasma collection container based, at least in part, on the monitored volume of collected plasma component.

6. A method according to claim 1, further comprising: monitoring a weight of plasma component collected within the plasma collection container, the calculated volume of pure plasma collected within the plasma collection container based, at least in part, on the monitored weight of collected plasma component.

7. A method according to claim 1, wherein step (b) includes monitoring a volume of red blood cells collected within the blood component separation device, the determined hematocrit of the donor based, at least in part, on the monitored volume of red blood cells collected within the blood component separation device and a volume of whole blood withdrawn from the donor.

8. A method according to claim 1, wherein the target volume of pure plasma is based, at least in part, on the weight of the donor.

9. A method according to claim 1, wherein the volume of anticoagulant in the collected plasma component includes at least a portion of the anticoagulant introduced into the withdrawn blood and at least a portion of a volume of anticoagulant added during a priming step.

10. A method according to claim 1, further comprising: returning, after collecting at least a portion of the target volume of pure plasma, the second blood component to the donor through a return line.

11. A system for collecting plasma comprising:
a venous-access device for drawing whole blood from a subject and returning blood components to the subject;
a blood component separation device for separating the drawn blood into a plasma component and a second blood component, the blood component separation device having an outlet and being configured to send the plasma component to a plasma container;
a blood draw line fluidly connected to the venous-access device and configured to transport drawn whole blood to the blood component separation device, the flow through the blood draw line being controlled by a blood draw pump;
an anticoagulant line connected to an anticoagulant source, the anticoagulant line configured to introduce anticoagulant into the drawn whole blood; and
a controller configured to control the operation of the blood component separation device and the blood draw pump, the controller configured to calculate (1) a volume of anticoagulant in the collected plasma component as the plasma component is being collected in the plasma container, and (2) a volume of pure plasma collected within the plasma container based, at least in part, upon the volume of anticoagulant in the collected plasma component, the controller configured to stop the blood draw pump when a target volume of pure plasma is collected within the plasma container.

12. A system according to claim 11, wherein the volume of anticoagulant in the collected plasma component is based, at least in part, on a volume of anticoagulant added to the drawn whole blood and the subject's hematocrit.

13. A system according to claim 11, further comprising:
an anticoagulant source weight sensor configured to measure the weight of the anticoagulant source, the controller further configured to monitor a change in volume within the anticoagulant source based on the measured weight of the anticoagulant source, the calculated volume of anticoagulant in the collected plasma component being based, at least in part, on the change in volume within the anticoagulant source.

14. A system according to claim 11, wherein the controller is configured to monitor a number of rotations of an anticoagulant pump to determine a volume of anticoagulant introduced into the whole blood, the calculated volume of anticoagulant in the collected plasma component being based, at least in part, on the number of rotations of the anticoagulant pump.

15. A system according to claim 11, further comprising:
an optical sensor located on the blood component separation device and configured to monitor the contents of the blood component separation device and determine if a volume of anticoagulant remains within the blood component separation device, the calculated volume of anticoagulant in the collected plasma component being based, at least in part, on the volume of anticoagulant within the blood component separation device.

16. A system according to claim 11, further comprising:
a plasma container weight sensor configured to monitor a volume of plasma component collected within the plasma container, the calculated volume of pure plasma collected within the plasma component based, at least in part, on the monitored volume of collected plasma component.

17. A system according to claim 11, further comprising:
a plasma container weight sensor configured to monitor a weight of plasma component collected within the plasma container, the calculated volume of pure plasma collected within the plasma component based, at least in part, on the monitored weight of collected plasma component.

18. A system according to claim 11, further comprising:
an optical sensor located on the blood component separation device and configured to monitor a volume of red blood cells collected within the blood component separation device, the controller configured to determine the subject's hematocrit based, at least in part, upon on the monitored volume of red blood cells collected within the blood component separation device and a volume of whole blood withdrawn from the subject.

19. A system according to claim 11, wherein the target volume of pure plasma is based, at least in part, on the weight of the subject.

20. A system according to claim 11, wherein the volume of anticoagulant in the collected plasma component includes at least a portion of the anticoagulant introduced into the withdrawn blood and at least a portion of a volume of anticoagulant added during a priming step.

* * * * *